United States Patent [19]

Beck et al.

[11] 4,153,730

[45] May 8, 1979

[54] FUNGICIDAL AND HERBICIDAL METHODS

[75] Inventors: James R. Beck; Robert P. Gajewski, both of Indianapolis, Ind.

[73] Assignee: Eli Lilly and Company, Indianapolis, Ind.

[21] Appl. No.: 817,469

[22] Filed: Jul. 20, 1977

[51] Int. Cl.² .............................................. A01N 9/20
[52] U.S. Cl. ..................................... 424/330; 71/106; 71/121
[58] Field of Search ......................................... 424/330

[56] References Cited

U.S. PATENT DOCUMENTS

| | | | |
|---|---|---|---|
| 3,119,736 | 1/1964 | Clark et al. | 424/330 |
| 3,948,957 | 4/1976 | Beck | 260/349 |
| 3,987,076 | 10/1976 | Beck | 260/454 |

FOREIGN PATENT DOCUMENTS 2161879 6/1973 Fed. Rep. of Germany.

OTHER PUBLICATIONS

Malichenko et al., Chem. Abst., vol. 73, (1970) 13451e.
Zsolnai Biochemical Pharmacology, vol. 5, (1961), pp. 287-304.
Buczacki, Ann. Appl. Biol. vol 75 (1973), pp. 25-30.
Eshel et al., Weed Science, vol. 20, (1972), pp. 243-246.

*Primary Examiner*—Catherine L. Mills
*Attorney, Agent, or Firm*—Dwight E. Morrison; Arthur R. Whale

[57] ABSTRACT

There are disclosed novel methods and compositions for the control of *Plasmopara viticola*, the causative organism of downy mildew of grape, and for the control of undesired vegetation, employing 2,6-dinitroanilines.

18 Claims, No Drawings

FUNGICIDAL AND HERBICIDAL METHODS

BACKGROUND OF THE INVENTION

1. Field of the Invention

This invention relates to the control of *Plasmopara viticola*, the causative organism of downy mildew of grape, and to the control of unwanted vegetation, using a class of 2,6-dinitroanilines.

2. Description of the Prior Art

Beginning in the early 1960's, Soper disclosed that 2,6-dinitroanilines possess herbicidal activity, most notably preemergent herbicidal activity. See, for example, U.S. Pat. Nos. 3,111,403; 3,257,190; 3,332,769; and 3,367,949. Following Soper's lead, a large number of related dinitroanilines have also been shown to possess similar herbicidal activity. See, for example, U.S. Pat. Nos. 3,321,292; 3,617,251, 3,617,252; 3,672,864; 3,672,866; 3,764,624; and 3,877,924 and Belgian Pat. No. 787,939. See also U.S. Pat. No. 3,725,479, for intermediate compounds.

Malichenko et al., *Fiziol. Aktiv. Veschestva* 1969, 2, 75-8; C.A. 73, 13451e (1970), disclose that some 2,6-dinitroanilines bearing a trifluoromethyl group in the 4-position possess some activity against *Phytophthora infestans*, the causative organism of late blight of tomato.

Clark et al., U.S. Pat. No. 3,119,736, disclose a broad class of compounds alleged to be fungicides. The generic description of such compounds includes dinitroanilines, but there is no specific disclosure of 2,6-dinitroanilines.

Zsolnai, *Biochemical Pharmacology* 5, 287-304 (1961), discloses that certain 2,4-dinitroanilines possess some fungicidal activity against various organisms. No 2,6-dinitroaniline was disclosed, nor was *Plasmopara viticola* among the organisms against which activity was shown.

Buczacki, *Ann. Appl. Biol.* 75, 25 (1973), tested five dinitroanilines against clubroot of cabbage with variable results. He concluded, however, that "dinitroanilines are unlikely to be of value in the control of clubroot."

Eshel and Katan, *Weed Science* 20, 243 (1972), observed the effects of four dinitroanilines against *Rhizoctonia solani* and *Fusarium oxysporum*. Three of the four test compounds decreased the growth of *R. solani* at the highest rates tested, but none of the four appreciably decreased the growth of *F. oxysporum* at any rate tested.

A study of trifluralin-treated soil by Breazeale and Camper, *Appl. Microbiol.* 19, 379 (1970), indicated that the actinomycete population increased as compared to the control, while the population of bacteria and fungi decreased.

A discussion of tests against the fungus *Lagenidium callinectes* is presented by Bland et al. in a paper entitled "Chemical Control of Lagenidium", an SEA Grant Publication UNC-SG-76-02, March 1976. The publication shows that some control of the fungus, which is a parasite of marine crustacea, is accomplished by application of TREFLAN (trifluralin) to water in which spores of the fungus were growing.

Yet another prior art reference is that of Nelson et al., Paper No. 59, entitled "Metabolism of Three Dinitroaniline Herbicides by Rat Liver Microsomes", Abstracts of Papers, 172nd National Meeting of the Chemical Society held in San Francisco, Aug. 29-Sept. 3, 1976. This reference discusses the metabolism in vitro by both normal and phenobarbital-induced rat liver microsomes of three closely related 14C-dinitroaniline herbicides, identified as trifluralin, fluchloralin, and profluralin. One of the metabolites is identified by Nelson et al. as "2,6-dinitro-N-(n-propan-2-ol)-N-propyl-$\alpha,\alpha,\alpha$-trifluoro-p-toluidine", also identified in the present application as 1-[[2,6-dinitro-4-(trifluoromethyl)phenyl]propylamino]-2-propanol. There is no teaching that these metabolites of known herbicides might themselves be herbicidal or fungicidal in their properties.

Also in the prior art, Beck, U.S. Pat. No. 3,948,957 (Apr. 6, 1976), discloses and claims compounds identified as 3-azido-2,6-dinitroanilines alleged to possess herbicidal activity and activity against *Plasmopara viticola*, the causative organism of grape downy mildew.

There is also in the prior art Beck, U.S. Pat. No. 3,987,076 (Oct. 19, 1976), which discloses and claims compounds identified as 2,6-dinitro-3-thiocyanatoanilines alleged to possess activity against *Plasmopara viticola*, the causative organism of grape downy mildew.

Another prior art reference is West German Offenlegungschrifft No. 2,161,879, published June 20, 1973, which teaches a method of preparing 2,6-dinitroaniline derivatives bearing hydroxyalkyl substituents on the amino nitrogen atom by reaction of a 2,6-dinitrochlorobenzene and amines and inorganic oxides. The compounds so produced are taught as being plant protection agents.

Two other references appearing in the prior art disclose and claim 2,6-dinitroaniline compounds having substituents in the 3-position, which compounds are alleged to be herbicides. See Lutz and Diehl, U.S. Pat. No. 3,920,742 (Nov. 18, 1975), and Lutz and Diehl, U.S. Pat. No. 4,025,538 (May 24, 1977).

SUMMARY OF THE INVENTION

The present invention relates to novel fungicidal and herbicidal compositions and to methods for the control of unwanted vegetation and for reducing the incidence and severity of grape downy mildew employing a 2,6-dinitroaniline selected from the group consisting of compounds of the formula:

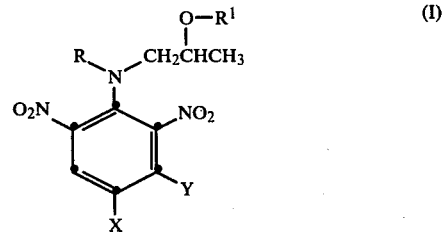

wherein
R is $C_1$–$C_4$ alkyl or $C_3$–$C_4$ alkenyl;
$R^1$ is hydrogen or

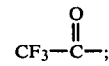

X is hydrogen, $C_1$–$C_4$ alkyl, trifluoromethyl, halo, or —$SO_2NH_2$; and
Y is hydrogen or amino;
with the exception that when $R^1$ is

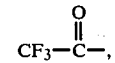

Y can only be hydrogen.

DESCRIPTION OF THE PREFERRED EMBODIMENTS

The present invention relates to novel fungicidal and herbicidal compositions, and to methods for the control of unwanted vegetation and for reducing the incidence and severity of grape downy mildew which comprises applying to the loci of unwanted vegetation or to the foliage of the host plant a herbicidally or fungicidally-effective amount of a compound of formula (I), above.

In one embodiment, this invention relates to a novel fungicidal method for reducing the incidence and severity of grape downy mildew which comprises applying to the foliage of the host plant a fungicidally-effective amount of a compound of the formula:

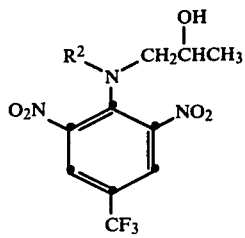
(II)

wherein
$R^2$ is $C_1$–$C_4$ alkyl or $C_3$–$C_4$ alkenyl.

In another embodiment of this invention, the novel fungicidal method for reducing the incidence and severity of grape downy mildew employs a fungicidally-effective amount of a compound of the formula:

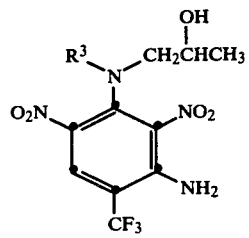
(III)

wherein
$R^3$ is methyl, ethyl, or n-propyl.

In yet another embodiment of this invention, the novel fungicidal method for reducing the incidence and severity of grape downy mildew employs a fungicidally-effective amount of a compound of the formula:

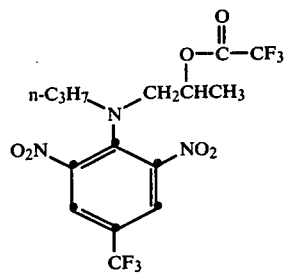
(IV)

In yet another embodiment of this invention, the novel fungicidal method employs a fungicidally-effective amount of a compound of the formula:

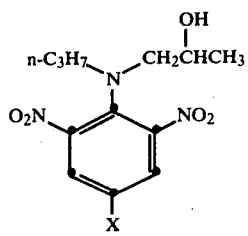
(V)

wherein
X is bromo or chloro.

Another embodiment of the novel fungicidal method employs a fungicidally-effective amount of a compound of the formula:

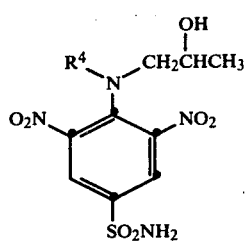
(VI)

wherein
$R^4$ is methyl, ethyl, n-propyl, or allyl.

Yet another embodiment of the novel fungicidal method of this invention for reducing the incidence and severity of grape downy mildew employs a fungicidally-effective amount of a compound of the formula:

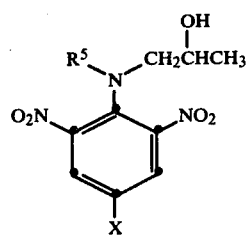
(VII)

wherein
$R^5$ is methyl, ethyl, n-propyl, or allyl; and
X is methyl, ethyl, isopropyl, or t-butyl.

Another embodiment of this invention of a novel method for reducing the incidence and severity of grape downy mildew employs a fungicidally-effective amount of a compound of the formula:

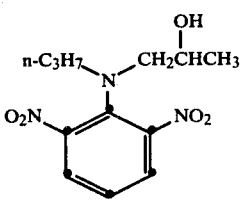
(VIII)

A particularly preferred embodiment of this invention is the method for reducing the incidence and severity of grape downy mildew which comprises applying to the foliage of the host plant a fungicidally-effective amount of a compound of the formula:

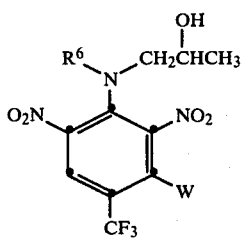

wherein
R⁶ is $C_1$-$C_4$ alkyl or $C_3$-$C_4$ alkenyl; and
W is hydrogen or amino.

In another embodiment, this invention relates to a novel method for controlling unwanted vegetation which comprises the preemergent application to the loci of the vegetation of a herbicidally-effective amount of a compound of the formula:

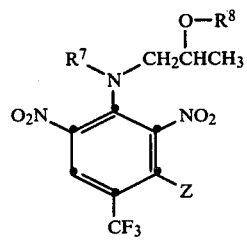
(IX)

wherein
R⁷ is ethyl, n-propyl, or allyl;
R⁸ is

or hydrogen; and
Z is hydrogen or amino;
with the exception that when R¹ is

Y can only be hydrogen.

In the above formulae, $C_1$-$C_4$ alkyl represents methyl, ethyl, n-propyl, isopropyl, n-butyl, sec-butyl, and t-butyl.

Also, $C_3$-$C_4$ alkenyl represents allyl, crotyl, or methallyl.

Halo represents bromo, chloro, fluoro, or iodo.

Although 2,6-dinitroanilines are well known in the herbicidal art, the majority of the compounds useful in the novel fungicidal and herbicidal methods of the instant invention are different from the prior art compounds due to the hydroxyl group in the alkylamino substituent, and most of the compounds have been first synthesized by us.

The compounds useful in this invention are synthesized according to one of the following general methods of preparation. In one method a suitably substituted 4-halo-3,5-dinitrobenzene is allowed to react with an appropriate amine in the presence of triethylamine in a suitable solvent. Suitable solvents include methanol, ethanol, and isopropyl alcohol. The reactants are mixed and stirred at a suitable reaction temperature to allow substantial completion of the reaction. The suitable reaction temperature varies from about ambient room temperature to the reflux temperature of the reaction mixture. Suitable times for reaction range from about ½ hour to about 26 hours.

At the end of the reaction time, the reaction mixture is allowed to cool and then is poured over ice and the solid product which precipitates is filtered off. This solid product is recrystallized then from a suitable solvent to yield the desired, purified product.

The 3-amino substituted compounds of this novel series are prepared from di-halo-3,5-dinitrobenzene compounds, which are known compounds. The method of synthesis is illustrated as follows. Thus, a suitably substituted di-halo-3,5-dinitrobenzene is allowed to react with an appropriate amine in the presence of triethylamine in dimethylformamide at about room temperature for about two hours or so. Anhydrous ammonia is then bubbled into the reaction mixture for about one minute with stirring. This treatment of the reaction mixture with ammonia is repeated at intervals for about 12 days, after which the reaction product mixture is worked up in the manner previously described for the des-amino compounds, and the product isolated and recrystallized.

The preparations of the compounds used in the novel methods and compositions of this invention are set forth hereinbelow.

Preparation 1

1-[(4-Bromo-2,6-dinitrophenyl)propylamino]-2-propanol

To a mixture containing 5.6 g. of 4-chloro-3,5-dinitrobromobenzene and 100 ml. of 95 percent ethanol, contained in a 250 ml. round bottomed flask, there was added 2.9 g. of N-propyl-N-(2-hydroxypropyl)amine and 2.5 g. of triethylamine. The reaction mixture was refluxed for about 24 hours. It was cooled and concentrated in vacuo on a rotary evaporator. The residue was chromatographed on a silica-gel column using toluene as the solvent and eluant. The eluant was collected and concentrated in vacuo on a rotary evaporator. The oil which remained was cooled and scratched, whereupon it crystallized. The crude crystalline material was recrystallized from hexane to yield product having a melting point of about 69°–70° C. weighing 2.9 g. The product was identified by elemental analyses and NMR and IR spectra.

Analyses calculated for $C_{12}H_{16}BrN_3O_5$:

|   | Theoretical | Found |
|---|---|---|
| C | 39.80 | 39.65 |
| H | 4.45 | 4.70 |

Following the same general procedure of Preparation 1, and using ethanol as the reaction solvent, additional compounds were prepared as follows:

Preparation 2

1-[(4-Methyl-2,6-dinitrophenyl)propylamino]-2-propanol, having a melting point of about 78°–81° C., and weighing 1.5 g., from 4.3 g. of 4-chloro-3,5-dinitrotoluene, 2.9 g. of N-propyl-N-(2-hydroxypropyl)amine, and 2.5 g. of triethylamine.

Analyses calculated for $C_{13}H_{19}N_3O_5$:

|   | Theoretical | Found |
|---|---|---|
| C | 52.52 | 52.29 |

-continued

Analyses calculated for $C_{13}H_{19}N_3O_5$:

| | Theoretical | Found |
|---|---|---|
| H | 6.44 | 6.32 |
| N | 14.13 | 14.02 |

Preparation 3

1-[[2,6-Dinitro-4-(trifluoromethyl)phenyl]-propylamino]-2-propanol, having a melting point of about 79°–81° C., and weighing 0.8 g., from 2.7 g. of 4-chloro-3,5-dinitrobenzotrifluoride, 2.4 g. of N-propyl-N-(2-hydroxypropyl)-amine, and 2.5 g. of triethylamine.

Analyses calculated for $C_{13}H_{16}F_3N_3O_5$:

| | Theoretical | Found |
|---|---|---|
| C | 44.45 | 44.65 |
| H | 4.59 | 4.76 |
| N | 11.96 | 12.05 |

Preparation 4

1-[(4-Ethyl-2,6-dinitrophenyl)propylamino]-2-propanol

A mixture was prepared in a 250 ml. round bottomed flask of 4.6 g. of 4-chloro-3,5-dinitroethylbenzene and 50 ml. of isopropyl alcohol. To this mixture was added 3.5 g. of N-propyl-N-(2-hydroxypropyl)amine and 3.0 g. of triethylamine. The mixture was refluxed for about 24 hours. The reaction product mixture was cooled and poured over a mixture of ice and water. The material which crystallized was filtered off and recrystallized from hexane to yield product having a melting point of about 73°–75° C. and weighing 3.8 g. The product was identified as 1-[(4-ethyl-2,6-dinitrophenyl)-propylamino]-2-propanol.

Analyses calculated for $C_{14}H_{21}N_3O_5$:

| | Theoretical | Found |
|---|---|---|
| C | 54.01 | 54.21 |
| H | 6.80 | 6.72 |
| N | 13.50 | 13.42 |

Following the same general procedure of preparation 4 and using isopropyl alcohol as the reaction solvent, additional compounds were prepared, as follows:

Preparation 5

1-[(4-Chloro-2,6-dinitrophenyl)propylamino]-2-propanol, having a melting point of about 87°–89° C., and weighing 4.6 g., from 4.7 g. of 1,4-dichloro-2,6-dinitrobenzene, 3.5 g. of N-propyl-N-(2-hydroxypropyl)amine, and 3.0 g. of triethylamine.

Analyses calculated for $C_{12}H_{16}ClN_3O_5$:

| | Theoretical | Found |
|---|---|---|
| C | 45.36 | 45.40 |
| H | 5.08 | 4.97 |
| N | 13.23 | 13.07 |

Preparation 6

1-[[4-(1,1-Dimethylethyl)-2,6-dinitrophenyl]-propylamino]-2-propanol, having a melting point of about 107°–109° C., and weighing 1.2 g., from 5.2 g. of 2,6-dinitro-4-t-butylchlorobenzene, 3.5 g. of N-propyl-N-(2-hydroxypropyl)amine, and 3.0 g. of triethylamine.

Analyses calculated for $C_{16}H_{25}N_3O_5$:

| | Theoretical | Found |
|---|---|---|
| C | 56.62 | 56.83 |
| H | 7.43 | 7.20 |
| N | 12.38 | 12.38 |

Preparation 7

1-[(2,6-Dinitrophenyl)propylamino]-2-propanol, having a melting point of about 76°–78° C., and weighing 2.3 g., from 4.1 g. of 1-chloro-2,6-dinitrobenzene, 3.5 g. of N-propyl-N-(2-hydroxypropyl)amine, and 3.0 g. of triethylamine.

Analyses calculated for $C_{12}H_{17}N_3O_5$:

| | Theoretical | Found |
|---|---|---|
| C | 50.88 | 50.69 |
| H | 6.05 | 5.79 |
| N | 14.83 | 14.58 |

Preparation 8

1-[[4-(1-Methylethyl)-2,6-dinitrophenyl]-propylamino]-2-propanol, having a melting point of about 52°–53° C., and weighing 3.0 g., from 4.9 g. of 2,6-dinitro-4-isopropylchlorobenzene, 3.5 g. of N-propyl-N-(2-hydroxypropyl)amine, and 3.0 g. of triethylamine.

Analyses calculated for $C_{15}H_{23}N_3O_5$:

| | Theoretical | Found |
|---|---|---|
| C | 55.37 | 55.38 |
| H | 7.13 | 6.95 |
| N | 12.92 | 12.75 |

Preparation 9

1-[Methyl(4-methyl-2,6-dinitrophenyl)amino]-2-propanol, having a melting point of about 106°–107° C., and weighing 3.8 g., from 4.3 g. of 4-chloro-3,5-dinitrotoluene, 2.7 g. of N-(2-hydroxypropyl)methylamine, and 3.0 g. of triethylamine.

Analyses calculated for $C_{11}H_{15}N_3O_5$:

| | Theoretical | Found |
|---|---|---|
| C | 49.07 | 49.00 |
| H | 5.62 | 5.38 |
| N | 15.61 | 15.47 |

Preparation 10

1-[Ethyl(4-methyl-2,6-dinitrophenyl)amino]-2-propanol, having a melting point of about 91°–93° C., and weighing 1.7 g., from 4.3 g. of 4-chloro-3,5-dinitrotoluene, 3.1 g. of N-(2-hydroxypropyl)ethylamine, and 3.0 g. of triethylamine.

Analyses calculated for $C_{12}H_{17}N_3O_5$:

| | Theoretical | Found |
|---|---|---|
| C | 50.88 | 50.79 |
| H | 6.01 | 5.93 |

| Analyses calculated for $C_{12}H_{17}N_3O_5$: | | |
|---|---|---|
| | Theoretical | Found |
| N | 14.84 | 14.69 |

Preparation 11

1-[(4-Methyl-2,6-dinitrophenyl)-2-propenylamino]-2-propanol, having a melting point of about 96°–99° C., and weighing 2.9 g., from 4.3 g. of 4-chloro-3,5-dinitrotoluene, 3.5 g. of N-allyl-(2-hydroxypropyl)amine, and 3.0 g. of triethylamine.

| Analyses calculated for $C_{13}H_{17}N_3O_5$: | | |
|---|---|---|
| | Theoretical | Found |
| C | 52.88 | 52.58 |
| H | 5.80 | 5.63 |
| N | 14.23 | 13.94 |

Preparation 12

1-[[3-Amino-2,6-dinitro-4-(trifluoromethyl)phenyl]ethylamino]-2-propanol

A mixture of 4.5 g. of 2,4-dichloro-3,5-dinitrobenzotrifluoride, 1.8 g. of N-(2-hydroxypropyl)ethylamine, 1.5 g. of triethylamine, and 40 ml. of dimethylformamide was prepared and was stirred at room temperature for about 2 hours. Anhydrous ammonia was then bubbled into the reaction mixture for about 1 minute with continued stirring. This treatment with ammonia was repeated at intervals for about 12 days. At the end of that time, the reaction product mixture was poured over crushed ice and the material which precipitated was filtered off and recrystallized from a mixture of ethanol and water to yield product having a melting point of about 114°–144° C. This material was chromatographed over silica-gel using a mixture of ethyl acetate and hexane in the ratio of 1:2 for further purification. The first fraction from the column was concentrated in vacuo and the residue thus obtained was recrystallized from ethanol. The product obtained had a melting point of about 110°–114° C. and weighed 1.5 g. It was identified by NMR and IR spectra and elemental analyses as 1-[[3-amino-2,6-dinitro-4-(trifluoromethyl)phenyl]ethylamino]-2-propanol.

| Analyses calculated for $C_{12}H_{15}F_3N_4O_5$: | | |
|---|---|---|
| | Theoretical | Found |
| C | 40.92 | 40.95 |
| H | 4.29 | 4.27 |
| N | 15.90 | 16.08 |

Following the same general procedure of the above Preparation 12, and using dimethylformamide as the reaction solvent, additional compounds were prepared, as follows:

Preparation 13

1-[[3-Amino-2,6-dinitro-4-(trifluoromethyl)phenyl]propylamino]-2-propanol, having a melting point of about 112°–114° C., and weighing 5.5 g., from 9.0 g. of 2,4-dichloro-3,5-dinitrobenzotrifluoride, 4.0 g. of N-(2-hydroxypropyl)propylamine, 3.0 g. of triethylamine, and ammonia.

| Analyses calculated for $C_{13}H_{17}F_3N_4O_5$: | | |
|---|---|---|
| | Theoretical | Found |
| C | 42.63 | 42.40 |
| H | 4.68 | 4.47 |
| N | 15.30 | 15.40 |

Preparation 14

1-[[3-Amino-2,6-dinitro-4-(trifluoromethyl)phenyl]methylamino]-2-propanol, having a melting point of about 165°–169° C., and weighing 0.8 g., from 9.2 g. of 2,4-dichloro-3,5-dinitrobenzotrifluoride, 3.0 g. of N-(2-hydroxypropyl)methylamine, 3.0 g. of triethylamine, and ammonia.

| Analyses calculated for $C_{11}H_{13}F_3N_4O_5$: | | |
|---|---|---|
| | Theoretical | Found |
| C | 39.06 | 38.88 |
| H | 3.87 | 3.83 |
| N | 16.56 | 16.53 |

Preparation 15

4-[(2-Hydroxypropyl)propylamino]-3,5-dinitrobenzenesulfonamide

A mixture of 8.5 g. of 4-chloro-3,5-dinitrobenzenesulfonamide, 4.2 g. of N-(2-hydroxypropyl)propylamine, 4.1 g. of potassium carbonate and 75 ml. of dimethylformamide was prepared and stirred at room temperature for about four hours. At the end of that time the reaction mixture was poured over 200 g. of crushed ice. The mixture was extracted with a mixture of ether and ethyl acetate and the extracts chromatographed over 500 g. of silica gel using a mixture of 1:1 ethyl acetate:-hexane as solvent and eluant. The eluate was concentrated and the product which was obtained had a melting point of about 121°–123° C., and weighed 1.5 g. The product was identified by elemental analyses as 4-[(2-hydroxypropyl)propylamino]-3,5-dinitrobenzenesulfonamide.

| Analyses calculated for $C_{12}H_{18}N_4O_7S$: | | |
|---|---|---|
| | Theoretical | Found |
| C | 39.78 | 40.04 |
| H | 5.01 | 5.07 |
| N | 15.46 | 15.19 |

Preparation 16

1-[[2,6-Dinitro-4-(trifluoromethyl)phenyl]methylamino]-2-propanol

A mixture of 5.4 g. of 4-chloro-3,5-dinitrobenzotrifluoride, 2.7 g. of N-(2-hydroxypropyl)methylamine, and 3.0 g. of triethylamine in 50 ml. of methanol was prepared in a 250 ml. round-bottomed flask and stirred for about 45 minutes. The reaction product mixture was poured over crushed ice and the solid which precipitated was filtered off. The solid was recrystallized from hexane to yield product having a melting point of about 61°–63° C., and weighing 4.0 g. The product was identified by elemental analyses as 1-[[2,6-dinitro-4-(trifluoromethyl)phenyl]methylamino]-2-propanol.

Analyses calculated for $C_{11}H_{12}F_3N_3O_5$:

|   | Theoretical | Found |
|---|---|---|
| C | 40.87 | 40.82 |
| H | 3.72 | 3.72 |
| N | 13.00 | 12.94 |

Following the same general procedure of Preparation 16, and using methanol as the reaction solvent, additional compounds were prepared, as follows:

Preparation 17

1-[[2,6-Dinitro-4-(trifluoromethyl)phenyl]ethylamino]-2-propanol, having a melting point of about 86°–87° C., and weighing 2.6 g., from 8.1 g. of 4-chloro-3,5-dinitrobenzotrifluoride, 3.7 g. of N-ethyl-N-(2-hydroxypropyl)amine, and 3.0 g. of triethylamine.

Analyses calculated for $C_{12}H_{14}F_3N_3O_5$:

|   | Theoretical | Found |
|---|---|---|
| C | 42.74 | 42.89 |
| H | 4.18 | 4.25 |
| N | 12.46 | 12.47 |

Preparation 18

1-[[2,6-Dinitro-4-(trifluoromethyl)phenyl]-2-propenylamino]-2-propanol, having a melting point of about 99°–100° C., and weighing 3.2 g., from 5.4 g. of 4-chloro-3,5-dinitrobenzotrifluoride, 3.5 g. of N-allyl-N-(2-hydroxypropyl)amine, and 3.0 g. of triethylamine.

Analyses calculated for $C_{13}H_{14}F_3N_3O_5$:

|   | Theoretical | Found |
|---|---|---|
| C | 44.71 | 44.80 |
| H | 4.04 | 3.75 |
| N | 12.03 | 12.19 |

Preparation 19

4-[(2-Hydroxypropyl)methylamino]-3,5-dinitrobenzenesulfonamide, having a melting point of about 164°–165° C., and weighing 6.3 g., from 11.3 g. of 4-chloro-3,5-dinitrobenzenesulfonamide, 5.4 g. of N-(2-hydroxypropyl)methylamine, and 6.0 g. of triethylamine.

Analyses calculated for $C_{10}H_{14}N_4O_7S$:

|   | Theoretical | Found |
|---|---|---|
| C | 35.93 | 36.17 |
| H | 4.22 | 4.00 |
| N | 16.76 | 16.61 |

Preparation 20

4-[Ethyl(2-hydroxypropyl)amino]-3,5-dinitrobenzenesulfonamide, having a melting point of about 160°–162° C., and weighing 9.3 g., from 11.3 g. of 4-chloro-3,5-dinitrobenzenesulfonamide, 6.2 g. of N-(2-hydroxypropyl)ethylamine, and 6.0 g. of triethylamine.

Analyses calculated for $C_{11}H_{16}N_4O_7S$:

|   | Theoretical | Found |
|---|---|---|
| C | 37.93 | 38.14 |
| H | 4.63 | 4.63 |
| N | 16.08 | 16.15 |

Preparation 21

1-[Butyl[2,6-dinitro-4-(trifluoromethyl)phenyl]amino]-2-propanol, having a melting point of about 78°–80° C., and weighing 6.2 g., from 10.8 g. of 4-chloro-3,5-dinitrobenzotrifluoride, 7.9 g. of N-(2-hydroxypropyl)butylamine, and 6.0 g. of triethylamine.

Analyses calculated for $C_{14}H_{18}F_3N_3O_5$:

|   | Theoretical | Found |
|---|---|---|
| C | 46.03 | 45.85 |
| H | 4.97 | 4.76 |
| N | 11.50 | 11.36 |

Preparation 22

4-[(2-Hydroxypropyl)-2-propenylamino]-3,5-dinitrobenzenesulfonamide, having a melting point of about 122°–123° C., and weighing 12.0 g., from 11.3 g. of 4-chloro-3,5-dinitrobenzenesulfonamide, 7.0 g. of N-allyl-N-(2-hydroxypropyl)amine, and 6.0 g. of triethylamine.

Analyses calculated for $C_{12}H_{16}N_4O_7S$:

|   | Theoretical | Found |
|---|---|---|
| C | 40.00 | 40.26 |
| H | 8.48 | 8.32 |
| N | 15.55 | 15.46 |

Preparation 23

Trifluoroacetic acid, 2-[[2,6-dinitro-4-(trifluoromethyl)phenyl]propylamino]-1-methylethyl ester A mixture was prepared of 1.05 g. of 1-[[2,6-dinitro-4-(trifluoromethyl)phenyl]propylamino]-2-propanol and 0.3 g. of triethylamine in 25 ml. of ether, and to this mixture there was added dropwise a solution of 0.65 g. of trifluoroacetic anhydride in 10 ml. of ether. The reaction product mixture was washed with water, dried, filtered from the drying agent and the ether evaporated. The solid material which remained was slurried with hexane and the slurry filtered. The solid product thus obtained had a melting point of about 94°–95° C., and weighed 1.1 g. The product was identified by elemental analyses and NMR and IR spectra as trifluoroacetic acid, 2-[[2,6-dinitro-4-(trifluoromethyl)phenyl]propylamino]-1-methylethyl ester.

Analyses calculated for $C_{15}H_{15}F_6N_3O_6$:

|   | Theoretical | Found |
|---|---|---|
| C | 40.28 | 40.49 |
| H | 3.38 | 3.42 |
| N | 9.39 | 9.96 |

To be utilized in the novel methods of the present invention, the above-described compounds may be formulated in novel compositions comprising one of the above-described compounds as the active ingredient and a solid or liquid carrier. Such novel compositions are useful and convenient for preparing the mixture desired for application to the loci of desired vegetation or fungus control. It is recognized that the particular type and concentration of formulation, as well as the mode of application of the active ingredient, may govern its biological activity in a given application.

Each active compound may be formulated as a simple solution in an appropriate solvent in which it is completely soluble at the desired concentration. Such solvent systems include alcohols, acetone, aqueous alcohol and aqueous acetone, xylene, heavy aromatic naphthas, and other organic solvents. These simple solutions may be further modified by the addition of various surfactants, emulsifying or dispersing agents, colorants, odorants, antifoaming agents, or other herbicides, herbicidal oils, or fungicides which supplement or synergize the respective activity of the compound being formulated.

The compounds useful in the present invention may also be formulated in various types of formulations commonly recognized by those skilled in the art of agricultural or industrial chemicals. These formulations include, for example, compositions containing the active ingredient as granules of relatively large particle size, as powder dusts, as wettable powders, as emulsifiable concentrates, or as a constituent part of any other known type of formulation commonly utilized by those skilled in the art. Such formulations include the adjuvants and carriers normally employed for facilitating the dispersion of an active ingredient for agricultural and industrial applications of fungitoxicants or phytotoxicants. These formulations may contain as little as 0.1% or as much as 90% by weight of the active ingredient.

Dust formulations are prepared by mixing the active ingredient with finely divided solids which act as dispersants and carriers for the phytotoxicant or fungitoxicant in applying it to the locus of desired vegetation control or fungus control. Typical solids which may be utilized in preparing dust formulations of the active ingredient useful in the invention include talc, kieselguhr, finely divided clay, fuller's earth, or other common organic or inorganic solids. Solids utilized in preparing dust formulations of the active ingredient normally have a particle size of 50 microns or less. The active ingredient of these dust formulations is present commonly in from as little as 0.5% to as much as 90% or more by weight of the composition.

Granular formulations of the active ingredient are prepared by impregnating or adsorbing the toxicant on or into relatively coarse particles of inert solids such as sand, attapulgite clay, gypsum, corncobs, vermiculite, or other inorganic or organic solids. The active ingredient of these granular formulations is commonly present in from 0.1% to as much as 90% or more by weight of the composition.

The compounds useful in the novel method of this invention may also be formulated as wettable powders. Wettable powder formulations are solid compositions of matter wherein the active ingredient is absorbed or adsorbed in or on a sorptive carrier such as finely divided clay, talc, gypsum, lime, wood flour, fuller's earth, kieserlguhr or the like. These formulations preferably are made to contain 0.5% to 90% of active ingredient. These wettable powder formulations commonly contain a small amount of a wetting, dispersing, or emulsifying agent to facilitate dispersion in water or other liquid carrier utilized to distribute the phytotoxicant or fungitoxicant to the locus of desired vegetation or fungus control. Suitable wetting and/or dispersing agents include condensed aryl sulfonic acids and sodium salts thereof, sodium lignosulfate, sulfonateoxide condensate blends, alkyl aryl polyether alcohols, sulfonated nonionic blends, anionic wetting agents, and the like. Suitable emulsifying agents can be of the nonionic or ionic types, or blends thereof, and include condensation products of alkylene oxides with phenols and organic acids, polyoxyethylene derivatives of sorbitan esters, complex ether-alcohols, ionics of the aralkyl sulfonate type, and the like.

The compounds usable in this invention may also be formulated as emulsifiable concentrates. Emulsifiable concentrate formulations are homogenous, liquid or paste compositions containing the active ingredient, which compositions will disperse in water or other liquid carrier to facilitate application of the phytotoxicant or fungitoxicant to the locus of desired vegetation control or fungi control. Such emulsifiable concentrate formulations of the active ingredients may contain only the active ingredient with a liquid or solid emulsifying agent, or may contain other relatively nonvolatile organic solvents such as isophorone, dioxane, heavy aromatic naphthas, xylene, or dimethylformamide. Emulsifying agents suitable for use in preparing these emulsifiable concentrate compositions are described in the immediately previous paragraph. The active ingredient in such a formulation commonly comprises from about 1% to about 70% by weight of the phytotoxicant or fungitoxicant composition.

The compounds usable in this invention may also be formulated in both pellet and tablet form.

The pellets are produced by combining the solid ingredients of the formulation in a suitable mixer, such as a ribbon blender, or the like. The active compound is placed in the blender together with one or more of a number of appropriate additives or excipients, such as clay, or a similar inert ingredient, a wetting agent, a dispersant, a lubricant, a binder, or the like, and the whole mixed with water. The mixture thus formed is transferred to the pellet mill for further processing. The size of the pellets is determined by the diameter of the die of the mill and the setting of the knives. After formation of the pellets, they are dried and screened to remove fines before packaging.

The tablet formulations are prepared by methods well-known to those skilled in the art of tablet preparation and who are knowledgeable in the field of agricultural chemicals. Thus, the active ingredient, that is, one of the compounds disclosed herein, is compounded with a suitable binder, other excipients and extenders, lubricants, and the like, the mixture granulated and compressed into tablets.

The formulation of agricultural chemicals is a well-developed art and those skilled in the art will have no difficulty in preparing formulations of active dinitroaniline compounds for use in the practice of the method of this invention.

The following experimental procedure was used to demonstrate the preemergent herbicidal activity of compounds coming within the scope of the generic formula of this application.

Trial 1

A soil was prepared consisting of one part masonry sand and one part shredded top soil blended together and then autoclaved. Plantings were made in galvanized metal flats which measure 31.5 cm. long, 21.5 cm. wide, and 8 cm. deep, with holes and grooves in the bottom for drainage. Each flat was filled two-thirds full with autoclaved soil and the soil was leveled and tamped. All the seeds were planted in rows perpendicular to the long axis of the flat. The preemergence application was tested in flats by planting the following seeds:

A. Corn (*Zea mays*)
B. Large crabgrass (*Digitaria sanguinalis*)
C. Pigweed (*Amaranthus retroflexus*)
D. Foxtail (*Setaria italica*)
E. (Velvetleaf (*Abutilon theophrasti*)
F. Morning glory (*Ipomoea purpurea*)
G. Zinnia (*Zinnia elegans*)

The preemergence flats were planted on the day of treatment and placed in the greenhouse. In the greenhouse, flats received 12 to 18 hours of light per day and were subject to temperatures of 75° to 85° F.

The compounds studied in this test were applied at the rate of 8.96 kg./ha., preemergent. The formulation for an application rate of 2.24 kg./ha. was accomplished by dissolving 60 mg. of the test compound in about 5 ml. of a solvent containing acetone and ethyl alcohol in a 1:1 ratio, together with a small amount of Toximul R and S. The solution was then diluted with deionized water to 12.5 ml., to provide the formulation for the application rate of 8.96 kg./ha. Toximul R and Toximul S are sulfonate/non-ionic blends which are products of Stepan Chemical Company, Northfield, Illinois.

The herbicidal compositions were applied to each flat with a modified DeVilbiss atomizer hooked to an air source. Twelve and one-half ml. of the composition under test was applied to each flat. One preemergent flat was treated for each compound. The preemergent flats were treated by surface application of the test solutions the day the seeds were planted.

The herbicidal effects of the chemicals were evaluated 15 days after treatment (DAT). The degree of plant injury is based on a 1 to 5 scale wherein 1 equals no injury and 5 equals 100% kill.

Table 1, which follows, sets forth the results of the preemergent testing of a number of the compounds coming within the scope of the generic formula, supra. In the table, column 1 identifies the compound by its operating example number in the application; and columns 2 through 7, the injury rating for particular plant species. The plant species are identified by letters of the alphabet.

Table 1

| | PLANT INJURY RATINGS 15 DAT AT 8.96 kg./ha. | | | | | | |
|---|---|---|---|---|---|---|---|
| | PREEMERGENCE | | | | | | |
| Compound | A | B | C | D | E | F | D |
| 1 | 1 | 4 | 4 | 4 | 1 | 2 | 1 |
| 2 | 1 | 3 | 4 | 4 | 2 | 3 | 2 |
| 3 | 3 | 4 | 5 | —* | 4 | 3 | 2 |
| 4 | 2 | 4 | 3 | 3 | 2 | 3 | 1 |
| 5 | 1 | 4 | 3 | 3 | 1 | 2 | 1 |
| 6 | 1 | 5 | 3 | 4 | 2 | 2 | 1 |
| 7 | 1 | 4 | 3 | 2 | 1 | 2 | 2 |
| 8 | 1 | 4 | 3 | 4 | 2 | 2 | 1 |
| 9 | 1 | 3 | 3 | 2 | 1 | 1 | 1 |
| 10 | 1 | 4 | 4 | 4 | 2 | 2 | 1 |
| 11 | 1 | — | 4 | 4 | 2 | 2 | 1 |
| 12 | 3 | 5 | 5 | 5 | 4 | 3 | 2 |
| 13 | 1 | 3 | 2 | 2 | 1 | 2 | 1 |
| 15 | 3 | 4 | 5 | 4 | 3 | 3 | 2 |
| 16 | 1 | 4 | 3 | 3 | 3 | 2 | 2 |
| 17 | 4 | 4 | 5 | 4 | 3 | 3 | 2 |

Table 1-continued

| | PLANT INJURY RATINGS 15 DAT AT 8.96 kg./ha. | | | | | | |
|---|---|---|---|---|---|---|---|
| | PREEMERGENCE | | | | | | |
| Compound | A | B | C | D | E | F | D |
| 18 | 1 | 4 | 4 | 4 | 2 | 2 | 1 |
| 19 | 1 | — | 2 | 3 | 2 | 1 | 1 |
| 20 | 2 | — | 4 | 4 | 3 | 2 | 2 |
| 21 | 1 | — | 4 | 4 | 2 | 1 | 1 |
| 22 | 2 | — | 4 | 4 | 2 | 2 | 2 |
| 23 | 3 | 4 | 4 | 5 | 3 | 3 | 1 |

*Not tested.

Trial 2

Further testing of certain of the compounds falling within the scope of the above generic formula as preemergent herbicides was carried out against a broader spectrum of plants. The plant species used in this experiment were planted in galvanized pans exactly like those used in Experiment 1, using the same type of soil. Each flat was filled two-thirds with the prepared soil and the soil leveled and tamped. In these preemergence tests, two flats containing ten indicator species each were used for each application rate of each chemical. The seeds of the species of plants were planted in rows parallel to the long axis of the flat, one species per half row, in the same manner as in Experiment 1. The approximate numbers of seeds planted are as follows:

A—Corn (*Zea mays*) 4
B—Cotton (*Gossypium hirsutum*) 6
C—Soybean (*Glycine max*) 6
D—Wheat (*Triticum aesitivum*) 40
E—Alfalfa (*Medicago sativa*) 100
F—Sugarbeet (*Beta vulgaris*) 25
G—Rice (*Oryza sativa*) 35
H—Cucumber (*Cucumis sativus*) 8
J—Tomato (*Lycopersicon esculentum*) 30
K—Barnyard grass (*Echinochloa crus-galli*) 50
L—Lambsquarter (*Chenopodium album*) 100
M—Large crabgrass (*Digitaria sanguinalis*) 100
N—Mustard (*Brassica juncea*) 50
O—Pigweed (*Amaranthus retroflexus*) 150
P—Foxtail millet (*Setaria italica*) 100
Q—Wild oat (*Avena fatua*) 25
R—Velvetleaf (*Abutilon theophrasti*) 25
S—Morning glory (*Ipomoea purpurea*) 15
T—Zinnia (*Zinnia elegans*) 20

For this preemergence testing, the flats were planted and the seeds covered with 0.5 to 1.0 cm. of soil, and on the same day as the planting, the treatments were applied. The chemicals were formulated the same way as described in Experiment 1 and then serially diluted to provide the desired concentrations of test solutions for applications at the desired rates. Chemicals were applied to the surface of the flats using a modified DeVilbiss atomizer connected to an air source. Each flat received 12.5 ml. of spray solution. The flats were maintained in the greenhouse after the treatment.

The herbicidal effects of the chemicals were evaluated about 18–21 days after these preemergence applications. The degree of plant injury is based on a 1 to 5 scale and a single numerical rating was assigned to each plant species as follows:

1 = no injury
2 = slight injury
3 = moderate injury
4 = severe injury

5=death

Table 2, which follows, sets forth the results of the preemergent testing of the compounds against crops, grasses, and broadleaf weeds. In the table, column 1 identifies the compound; column 2, the rate in terms of kg./ha. at which the compound was applied to the test flat; and the remainder of the columns, the injury ratings for the particular plant seedlings.

plastic petri plate containing a Whatman filter paper placed on top of an expanded plastic mat to keep the leaf above the water flooding the bottom of the petri plate. A water-soaked wad of cotton was wrapped around the petiole base of the leaf. The test chemical at the desired concentration was sprayed on the underside of the leaf to run off and the leaf allowed to dry. As soon as the leaf dried, it was innoculated by spraying Table 2

| | | Preemergence Plant Injury Ratings | | | | | | | | | | | | | | | | | | | |
|---|---|---|---|---|---|---|---|---|---|---|---|---|---|---|---|---|---|---|---|---|---|
| Compound | Appln. Rate kg./ha. | A | B | C | D | E | F | G | H | I | J | K | L | M | N | O | P | Q | R | S | T |
| 1 | 1.12 | 1 | 1 | 1 | 1 | 1 | 1 | 1 | 1 | 1 | 3 | 1 | 3 | 1 | 2 | 1 | 1 | 1 | 1 | 1 | 1 |
|   | 2.24 | 1 | 1 | 1 | 1 | 1 | 1 | 1 | 1 | 1 | 4 | 1 | 3 | 1 | 2 | 2 | 1 | 1 | 1 | 1 | 1 |
|   | 4.48 | 1 | 1 | 1 | 1 | 1 | 1 | 1 | 1 | 1 | 4 | 2 | 4 | 1 | 3 | 4 | 3 | 2 | 1 | 1 | 1 |
| 2 | 1.12 | 1 | 1 | 1 | 1 | 1 | 2 | 3 | 1 | 1 | 3 | 1 | 2 | 1 | 2 | 2 | 1 | 1 | 1 | 1 | 1 |
|   | 2.24 | 1 | 1 | 1 | 1 | 1 | 2 | 3 | 1 | 1 | 3 | -* | 3 | 2 | - | 3 | 1 | 1 | 1 | 1 | 1 |
|   | 4.48 | 1 | 1 | 1 | 1 | 1 | 3 | 3 | 1 | 2 | 3 | 2 | 4 | 2 | 2 | 4 | 2 | 1 | 1 | 2 | 1 |
| 3 | 1.12 | 1 | 1 | 1 | 1 | 1 | 3 | 2 | 1 | 2 | 4 | 1 | 4 | 2 | 3 | 4 | 3 | 2 | 1 | 2 | 1 |
|   | 2.24 | 1 | 1 | 1 | 2 | 3 | 2 | 3 | 2 | 2 | 4 | 3 | 5 | 2 | 4 | 4 | 3 | 2 | 1 | 2 | 1 |
|   | 4.48 | 2 | 1 | 1 | 2 | 4 | 3 | 4 | 3 | 3 | 5 | 3 | 5 | 1 | 5 | 4 | 4 | 4 | 1 | 2 | 2 |
| 6 | 1.12 | 1 | 1 | 2 | 1 | 1 | 1 | 1 | 1 | 2 | 3 | 3 | — | 1 | 1 | 3 | 1 | 1 | 1 | 1 | 1 |
|   | 2.24 | 1 | 1 | 1 | 1 | 1 | 2 | 1 | 1 | 2 | 3 | 3 | — | 1 | 2 | 3 | 2 | 1 | 1 | 1 | 1 |
|   | 4.48 | 2 | 1 | 1 | 1 | 2 | 2 | 1 | 2 | 2 | 4 | 3 | — | 1 | 3 | 4 | 3 | 2 | 2 | 1 | 1 |
| 8 | 1.12 | 1 | 1 | 1 | 1 | 1 | 1 | 2 | 1 | 3 | 2 | 2 | — | 1 | 2 | 3 | 1 | 1 | 1 | 1 | 1 |
|   | 2.24 | 1 | 1 | 1 | 1 | 1 | 1 | 1 | 2 | 2 | 2 | 3 | — | 1 | 2 | 2 | 2 | 1 | 1 | 1 | 1 |
|   | 4.48 | 2 | 1 | 1 | 1 | 2 | 3 | 2 | 1 | 3 | 2 | 3 | — | 1 | 3 | 3 | 2 | 1 | 1 | 2 | 1 |
| 10 | 1.12 | 1 | 1 | 1 | 1 | 1 | 1 | 1 | 1 | 1 | 2 | 1 | 1 | 1 | 1 | 3 | 2 | 2 | 1 | 1 | 1 |
|   | 2.24 | 1 | 1 | 1 | 1 | 1 | 1 | 1 | 1 | 2 | 1 | 3 | 3 | 2 | 3 | 3 | 1 | 2 | 2 | 1 | 1 |
|   | 4.48 | 1 | 1 | 1 | 1 | 1 | 2 | 2 | 1 | 2 | 3 | 3 | 3 | 2 | 3 | 1 | 1 | 1 | 2 | 1 | 1 |
| 11 | 4.48 | 1 | 1 | 1 | 1 | 1 | 1 | 3 | 1 | 1 | 4 | 1 | 3 | 1 | 2 | 1 | 1 | 1 | 1 | 1 | 1 |
| 12 | 1.12 | 3 | 1 | 2 | 2 | 4 | 4 | 4 | 3 | 3 | 4 | 4 | 4 | 3 | 4 | 5 | 3 | 3 | 2 | 3 | 2 |
|   | 2.24 | 4 | 3 | 3 | 2 | 4 | 4 | 4 | 3 | 3 | 4 | 4 | 5 | 3 | 4 | 5 | 4 | 3 | 2 | 3 | 1 |
|   | 4.48 | 4 | 3 | 3 | 3 | 5 | 4 | 4 | 4 | 4 | 5 | 4 | 5 | 4 | 4 | 5 | 4 | 4 | 2 | 4 | 3 |
| 15 | 1.12 | 1 | 1 | 1 | 1 | 1 | 3 | 1 | 1 | 2 | 1 | 1 | — | 1 | 2 | 1 | 1 | 1 | 1 | 1 | 1 |
|   | 2.24 | 1 | 1 | 1 | 1 | 1 | 2 | 1 | 1 | 2 | 1 | 2 | — | 1 | 4 | 2 | 1 | 2 | 1 | 1 | 1 |
|   | 4.48 | 1 | 2 | 1 | 1 | 2 | 2 | 1 | 2 | 2 | 3 | 2 | — | 1 | 3 | 3 | 2 | 2 | 1 | 1 | 1 |
| 17 | 1.12 | 1 | 1 | 1 | 1 | 1 | 1 | 2 | 1 | 1 | 3 | 2 | 3 | 1 | 3 | 3 | 3 | 2 | 1 | 1 | 1 |
|   | 2.24 | 1 | 1 | 1 | 1 | 1 | 1 | 2 | 1 | 1 | 4 | 2 | 4 | 2 | 4 | 4 | 3 | 2 | 1 | 1 | 2 |
|   | 4.48 | 1 | 1 | 1 | 1 | 1 | 1 | 3 | 1 | 1 | 5 | 3 | 5 | 2 | 5 | 4 | 3 | 2 | 1 | 1 | 2 |
| 18 | 1.12 | 1 | 1 | 1 | 1 | 1 | 2 | 1 | 1 | 2 | 1 | 3 | 2 | 1 | 2 | 2 | 1 | 1 | 1 | 1 | 1 |
|   | 2.24 | 1 | 1 | 1 | 1 | 1 | 2 | 2 | 1 | 2 | 2 | 1 | 3 | 1 | 2 | 3 | 3 | 2 | 1 | 1 | 1 |
|   | 4.48 | 1 | 1 | 1 | 1 | 1 | 3 | 2 | 1 | 2 | 3 | 3 | 3 | 1 | 2 | 3 | 3 | 2 | 2 | 1 | 1 |
| 21 | 1.12 | 1 | 1 | 1 | 1 | 1 | 1 | 2 | 1 | 1 | 3 | 1 | 3 | 1 | 2 | 3 | 1 | 1 | 1 | 1 | 1 |
|   | 2.24 | 1 | 1 | 1 | 1 | 1 | 1 | 1 | 1 | 1 | 3 | 1 | 4 | 1 | 2 | 3 | 1 | 1 | 1 | 1 | 1 |
|   | 4.48 | 1 | 1 | 1 | 1 | 1 | 1 | 1 | 1 | 1 | 3 | 1 | 4 | 1 | 1 | 3 | 1 | 1 | 1 | 1 | 1 |
| 23 | 1.12 | 1 | 1 | 1 | 1 | 2 | 1 | 2 | 1 | 1 | 3 | 1 | 3 | 1 | 3 | 3 | 1 | 1 | 1 | 1 | 1 |
|   | 2.24 | 1 | 1 | 1 | 1 | 2 | 2 | 3 | 1 | 1 | 3 | 1 | 3 | 1 | 3 | 3 | 2 | 3 | 1 | 1 | 1 |
|   | 4.48 | 1 | 1 | 1 | 1 | 2 | 2 | 3 | 1 | 2 | 3 | 1 | 4 | 1 | 4 | 4 | 3 | 3 | 1 | 1 | 1 |

*Not tested

Trial 3

The usefulness of the compounds of this invention to reduce the incidence and severity of grape downy mildew was also demonstrated in greenhouse tests. The test compounds were formulated by mixing 70 mg. of the compound with 2 ml. of a solution prepared from 500 ml. of acetone, 500 ml. of ethanol, and 100 ml. of Tween 20. (Tween 20 is a polyoxyethylene sorbitan monolaurate made by Atlas Chemical Division of ICI America, Inc., Wilmington, Delaware.) The sample was then diluted with 175 ml. of deionized water containing one drop of Dow Corning antifoam C emulsion per 2 l. of water. (Dow Corning antifoam C is a silicone complex antifoaming agent made by Dow Corning Corporation, Midland, Michigan.) The final formulation contains 400 ppm. of the test compound, 10,000 ppm. of organic solvents, and 1,000 ppm. of Tween 20. This solution was diluted with deionized water to obtain the lower concentration of the particular test compound.

On the day the test was started, young expanding leaves were detached from grape vines grown in the greenhouse. One leaf was placed bottom side up in a with a conidial suspension of *Plasmopara viticola* using a DeVilbiss sprayer. The conidial suspension was prepared as follows. Conidia were obtained from recently infected leaf tissue stored in the chill room at 5° C. The conidia were washed off the leaf's surface with a brush and suspended in deionized water to obtain the innoculation suspension.

After innoculation the plates were placed in a moist chamber. Cool white fluorescent lamps above the moist chamber hood provided 200 to 400 foot-candles of light to the leaves on a cycle of 14 hours of light and 10 hours of darkness at 68° F. The leaves were observed for disease symptoms and the results were recorded seven days after treatment. A rating scale of 1 to 5 was used to record the results where 1 equals severe disease (or no control), 2 equals moderate disease, 3 equals slight disease, 4 equals very slight disease, and 5 equals no disease (or 100% control).

The results of testing representative compounds of this invention are reported in Table 3. In the table, column 1 identifies the test compounds by operating example number; and columns 2, 3 and 4 list the disease control ratings at the indicated ppm. application rates.

Table 3

| | Activity Against Grape Downy Mildew | | |
|---|---|---|---|
| | Application Rate | | |
| Compound No. | 400 | 200 | 100 |
| 1 | 5 | | 5 |
| 2 | 5 | | 5 |
| 3 | * | 5 | 5 |
| 4 | 5 | | 5 |
| 5 | 5 | | 5 |
| 6 | 5 | | 5 |
| 7 | 5 | | 5 |
| 8 | 5 | | 5 |
| 9 | 4 | | 3 |
| 10 | 5 | | 5 |
| 11 | 5 | | 5 |
| 12 | 5 | | 5 |
| 13 | 5 | | 5 |
| 14 | 5 | | 5 |
| 15 | 3 | | 4 |
| 16 | 5 | | 5 |
| 17 | 5 | | 5 |
| 18 | 5 | | 5 |
| 19 | 3 | | 5 |
| 20 | 4 | | 3 |
| 21 | 5 | | 5 |
| 22 | 4 | | 4 |

*Not tested at this level.

The above described tests and results show the compounds disclosed herein to be useful in the novel fungicidal or herbicidal method hereinabove disclosed.

The exact concentration of the dinitroaniline compound for use in the control of phytopathogens can vary widely provided that an effective amount is applied to the host plant. The amount which is effective is dependent upon the particular compound employed and the severity of the infection. In general, good results are obtained using liquid compositions containing from about 2,000 to about 10 ppm. of the active compound. When dusts are used, good results are usually obtained with compositions containing from about 0.05 to 5.0% or more by weight of the active compound. Preferably, the compounds are applied at a rate of from about 10 g. to about 2 kg. per hectare.

We claim:

1. A method for reducing the incidence and severity of grape downy mildew which comprises applying to the foliage of the host plant a fungicidally-effective amount of a compound of the formula

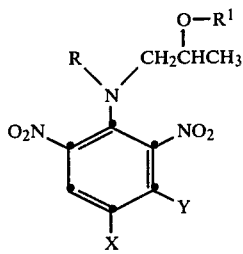

wherein
R is $C_1$–$C_4$ alkyl or $C_3$–$C_4$ alkenyl;
$R^1$ is hydrogen or

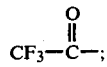

X is hydrogen, $C_1$–$C_4$ alkyl, trifluoromethyl, halo, or —$SO_2NH_2$; and
Y is hydrogen or amino;
with the exception that when $R^1$ is

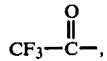

Y can only be hydrogen.

2. The method of claim 1 wherein the active compound is 1-[(4-bromo-2,6-dinitrophenyl)propylamino]-2-propanol.

3. The method of claim 1 wherein the active compound is 1-[(4-methyl-2,6-dinitrophenyl)propylamino]-2-propanol.

4. The method of claim 1 wherein the active compound is 1-[[2,6-dinitro-4-(trifluoromethyl)phenyl]propylamino]-2-propanol.

5. The method of claim 1 wherein the active compound is 1-[(4-ethyl-2,6-dinitrophenyl)propylamino]-2-propanol.

6. The method of claim 1 wherein the active compound is 1-[(4-chloro-2,6-dinitrophenyl)propylamino]-2-propanol.

7. The method of claim 1 wherein the active compound is 1-[[4-(1,1-dimethylethyl)-2,6-dinitrophenyl]propylamino]-2-propanol.

8. The method of claim 1 wherein the active compound is 1-[(2,6-dinitrophenyl)propylamino]-2-propanol.

9. The method of claim 1 wherein the active compound is 1-[[4-(1-methylethyl)-2,6-dinitrophenyl]propylamino]-2-propanol.

10. The method of claim 1 wherein the active compound is 1-[ethyl(4-methyl-2,6-dinitrophenyl)amino]-2-propanol.

11. The method of claim 1 wherein the active compound is 1-[(4-methyl-2,6-dinitrophenyl)-2-propenylamino]-2-propanol.

12. The method of claim 1 wherein the active compound is 1-[[3-amino-2,6-dinitro-4-(trifluoromethyl)phenyl]ethylamino]-2-propanol.

13. The method of claim 1 wherein the active compound is 1-[[3-amino-2,6-dinitro-4-(trifluoromethyl)phenyl]propylamino]-2-propanol.

14. The method of claim 1 wherein the active compound is 1-[[3-amino-2,6-dinitro-4-(trifluoromethyl)phenyl]methylamino]-2-propanol.

15. The method of claim 1 wherein the active compound is 1-[[2,6-dinitro-4-(trifluoromethyl)phenyl]methylamino]-2-propanol.

16. The method of claim 1 wherein the active compound is 1-[[2,6-dinitro-4-(trifluoromethyl)phenyl]ethylamino]-2-propanol.

17. The method of claim 1 wherein the active compound is 1-[[2,6-dinitro-4-(trifluoromethyl)phenyl]-2-propenylamino]-2-propanol.

18. The method of claim 1 wherein the active compound is 1-[butyl[2,6-dinitro-4-(trifluoromethyl)phenyl]amino-2-propanol.